(12) United States Patent
Grigoriou et al.

(10) Patent No.: US 10,219,964 B2
(45) Date of Patent: Mar. 5, 2019

(54) TRANSPORT AND STORAGE SYSTEM FOR SERVICING OF A NUMBER OF TREATMENT AND CARE AREAS IN A HOSPITAL AND METHOD FOR OPERATION HEREOF

(71) Applicant: INTELLIGENT SYSTEMS A/S, Hadsund (DK)

(72) Inventors: Niki Nicolas Grigoriou, Hadsund (DK); Ole Nielsen, Aalborg (DK)

(73) Assignee: INTELLIGENT SYSTEMS A/S, Hadsund (DK)

( * ) Notice: Subject to any disclaimer, the term of this patent is extended or adjusted under 35 U.S.C. 154(b) by 0 days.

(21) Appl. No.: 15/553,832

(22) PCT Filed: Feb. 8, 2016

(86) PCT No.: PCT/DK2016/050033
§ 371 (c)(1),
(2) Date: Aug. 25, 2017

(87) PCT Pub. No.: WO2016/134721
PCT Pub. Date: Sep. 1, 2016

(65) Prior Publication Data
US 2018/0036192 A1     Feb. 8, 2018

(30) Foreign Application Priority Data

Feb. 27, 2015   (DK) .................................. 2015 70111

(51) Int. Cl.
*B65G 35/06*      (2006.01)
*A61G 12/00*      (2006.01)

(52) U.S. Cl.
CPC ........... *A61G 12/002* (2013.01); *A61G 12/00* (2013.01); *B65G 35/06* (2013.01)

(58) Field of Classification Search
CPC ..................................................... B65G 35/06
(Continued)

(56) References Cited

U.S. PATENT DOCUMENTS

| 3,453,659 A | | 7/1969 | Beecher et al. | |
| 3,743,116 A | * | 7/1973 | Giessler | B65G 37/00 |
| | | | | 104/165 |

(Continued)

FOREIGN PATENT DOCUMENTS

| DE | 3641594 A1 | 6/1987 |
| EP | 208298 A1 | 7/2009 |
| GB | 2195597 A | 4/1988 |

OTHER PUBLICATIONS

Pedersen et al., "Staff Safety Guidelines for Interior Health / Northern Health Facility Design Projects," Northern Health, Nov. 2014, pp. 1-49.

(Continued)

*Primary Examiner* — Joseph A Dillon, Jr.
(74) *Attorney, Agent, or Firm* — Birch, Stewart, Kolasch & Birch, LLP

(57) ABSTRACT

A transport and storage system, for servicing of a number of treatment and care areas in a hospital, is provided. The system connects each treatment and care area to a first transport route reserved for transport of clean goods to or from the treatment and care area, and a second transport route reserved for transport of non-clean goods to or from the treatment and care area, the first and second transport routes being separated. In the system, a partition is provided between the transport routes and the treatment and care areas, with a lock gate being included in the partition. The transport routes include a conveyor to containers, with the conveyor being connected to the lock gate and the containers having a container brim enclosable by an opening in the lock gate.

2 Claims, 7 Drawing Sheets

Figure 1:
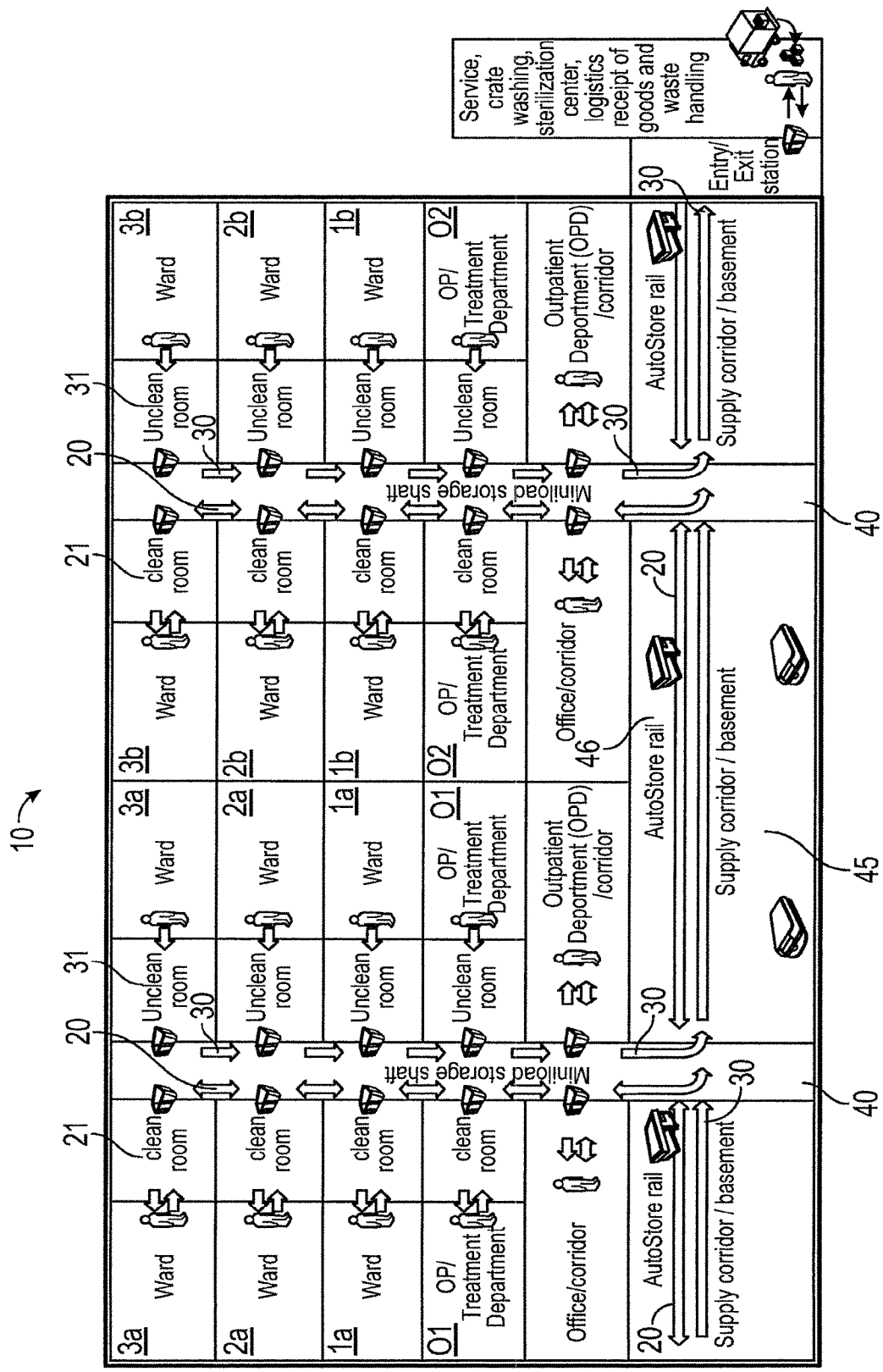

(58) Field of Classification Search
USPC .................................................. 414/221, 277
See application file for complete search history.

(56) References Cited

U.S. PATENT DOCUMENTS

| | | | | |
|---|---|---|---|---|
| 3,857,463 | A * | 12/1974 | Wagenfuhrer | A47F 10/06 186/49 |
| 4,279,563 | A | 7/1981 | Miller | |
| 4,588,343 | A * | 5/1986 | Garrett | H01L 21/68735 204/298.25 |
| 4,817,694 | A | 4/1989 | Matsuo et al. | |
| 4,948,979 | A * | 8/1990 | Munakata | H01J 37/18 250/441.11 |
| 4,966,513 | A * | 10/1990 | Motoda | B65G 1/02 414/277 |
| 5,000,641 | A * | 3/1991 | Kikuchi | B65F 1/0093 414/21 |
| 5,297,917 | A * | 3/1994 | Freneix | B61L 3/227 246/30 |
| 5,487,636 | A * | 1/1996 | Mkrtchyan | B65G 1/0435 414/245 |
| 6,358,377 | B1 * | 3/2002 | Schloremberg | C03C 17/002 118/719 |
| 6,394,733 | B1 * | 5/2002 | Toda | H01L 21/67017 406/192 |
| 6,457,928 | B1 * | 10/2002 | Ryan | G11B 15/6825 312/9.1 |
| 6,517,691 | B1 * | 2/2003 | Bluck | C23C 14/568 118/719 |
| 7,039,499 | B1 * | 5/2006 | Nasr | B25J 9/046 206/710 |
| 7,931,431 | B2 * | 4/2011 | Benedict | B63B 25/22 280/755 |
| 8,025,473 | B2 * | 9/2011 | Asakawa | H01L 21/67727 198/346.2 |
| 8,388,296 | B2 * | 3/2013 | Suzuki | H01L 21/67769 414/221 |
| 8,443,513 | B2 * | 5/2013 | Ishida | H01L 21/67051 29/771 |
| 9,020,632 | B2 * | 4/2015 | Naylor | B65G 1/065 414/273 |
| 9,532,685 | B2 * | 1/2017 | Schaaf | A47K 11/02 |
| 9,815,624 | B2 * | 11/2017 | Yoshioka | B65G 1/06 |
| 2003/0093176 | A1 | 5/2003 | Ohtsuka et al. | |
| 2007/0025830 | A1 * | 2/2007 | Solomon | A47B 63/067 414/217 |
| 2008/0003081 | A1 * | 1/2008 | Kasumi | H01L 21/67748 414/217 |
| 2008/0247845 | A1 * | 10/2008 | Mochizuki | H01L 21/67017 414/217.1 |
| 2010/0202860 | A1 * | 8/2010 | Reed | H01L 21/68742 414/221 |
| 2011/0176895 | A1 * | 7/2011 | Kortelainen | B65G 1/0435 414/277 |
| 2013/0236278 | A1 * | 9/2013 | Beewen | B65G 1/0492 414/278 |
| 2014/0003894 | A1 * | 1/2014 | Takahara | B60S 11/00 414/277 |
| 2014/0182242 | A1 * | 7/2014 | Winkler | A47F 10/00 53/235 |
| 2014/0241837 | A1 * | 8/2014 | Bartelet | B65G 1/10 414/277 |

OTHER PUBLICATIONS

Department of Veterans Affairs, Ofice of Facilities Management, Design Guide, Aug. 2005.

* cited by examiner

TRANSPORT AND STORAGE SYSTEM FOR SERVICING OF A NUMBER OF TREATMENT AND CARE AREAS IN A HOSPITAL AND METHOD FOR OPERATION HEREOF

The invention relates to a transport and storage system for servicing of a number of treatment and care areas in a hospital.

Moreover, the invention relates to a method for operation of transport and storage system for servicing of a number of treatment and care areas in a hospital.

From "Interior health authority, British Columbia, Canada: Pedersen, R. et al: Staff Safety Guidelines For Interior Health/Northern Health Facility Design Projects Updated November 2014" it is known that elevators to and from patient treatment areas should be divided into clean elevators, which lead to the area and non-clean elevators, which lead away from the area. From "Department of Veteran Affairs, Office of Facilities Management Design Guide for Surgical Service. August 2005" is known a similar specification for freight elevators to and from operation rooms.

From U.S. Pat. No. 4,279,563 A is known a transport system to a hospital with a separation between transport trolleys towards patient departments and trolleys headed away from patient departments.

In hospitals, there is a quite large flow of goods to and from the patient treating sections, also called "ward" or "treatment or care areas" in the subsequent. Besides the more mundane such as food and bed linen, there are a wide range of special products, which must each day be added to the individual departments according to their function. Simultaneously, there is a flow of articles, which are either trash or are reusable objects, which must be transported from the department and to washing or other upgrading. It concerns used tableware and linen but also operation equipment, which must be cleaned and autoclaved for the next operation. Furthermore, there exists special transports, such as for example transport of biological samples and transport of medicine from the hospital's pharmacy and out to the patients. In today's hospitals there exists different solutions to these tasks, such as for example air tube systems for medicine and biological samples. There is also known automatic trolley units for transport of beds or linen, which are typically designed to be in areas without patient influx. Finally, much transport is based on ordinary manual freight with simple trolleys and pallet jacks or similar vehicles, which are pushed by hand around the hospital. There is here a significant risk of clean, and in principle sterile material, headed towards a ward, being stored en route in the same room, side by side with used material, which poses a risk of infection and is headed away from a ward. The different trolleys or storage units can cross each other's way and there can occur mixture also across individual wards.

With the invention, a transport system is provided where the risk of infection from used materials or materials, which are transported away from a care and treatment area, is minimized to the highest extent.

This occurs by a transport route being connected to each treatment and care area, which is reserved for delivery of clean goods for the treatment and care area and a transport route, which is reserved for removal of non-clean goods from the treatment and care area, where the two transport routes are separated, since a partition is provided between the transport routes and the treatment and care areas and where there in the partition is a lock gate and the transport routes include a conveyor to containers, which conveyor is connected to the lock gate since the container has a container brim and the lock gate has a, to the container brim, enclosing lock opening. Hereby, an actual separation is made possible, not just of the transport routes from the treatment and care areas, but also between the transported material and the transport routes as such, since all material is subsequently transported in the containers and the container's exterior is never in actual contact with the treatment and care areas, since it is only the inner of the containers, which via the lock gate is made accessible from here.

According to an embodiment, a lid belongs to the container brim, which is designed for enclosing mesh with the container brim, whereby it is ensured that the content in a specific container is not in contact with the surroundings during the transport.

According to an embodiment, the lock gate includes a gripper for separation of container and belonging lid, such that the container's inner is made accessible from the treatment and care areas when a given container is led to a given lock gate. With such an arrangement, it is ensured that personnel and patients do not have a need to contact the container's exterior during any part of the task of filling or emptying hereof. A container's lid is taken off automatically by the gripper, for example via movable parts, which can grip around a protruding flange on the lid such that the lid, subsequently automatically and without contact with the personnel, is removed from its mesh with the container opening.

According to an embodiment, there is used two different types of containers, a first type for transport of material to, and another type for transport away from, the treatment and care areas. Hereby, the two types of containers can be manufactured and optimized according to each own function. For example, the containers, which are to receive trash and used material and thereby be used on the non-clean transport route, should have an opening, which faces upwards, where the containers, which are used on the clean transport route and are used for transport of goods towards a ward, can quite well have an opening in a vertical side surface.

According to an embodiment, the invention relates to a method for operation of transport and storage system for servicing of a number of treatment and care areas in a hospital. According to the invention, there is thus, to each care area, connected a clean transport route for delivery of goods to the treatment and care area and a non-clean transport route for removal of goods from the treatment and care area, where the two transport routes are separated and furthermore, all transport routes and all storage areas for containers are in connection with a computer system. This system emits signals in order to initialize the clean transport route for moving of a container containing clean material towards the treatment and care area and emits signals in order to initialize the non-clean transport route for moving of containers containing non-clean material away from a treatment and care area. The transport routes, which are here mentioned, can for example consist of robot trolleys, which can transport a container in both the one and the other direction and if a container is thus moved towards or away from a treatment and care area therefore depends on which control signals the trolleys receive. Each transport route must handle both filled and empty containers since the clean, but empty containers must be sent away from treatment and care areas for washing and renewed filling and this will typically occur on the transport route for clean containers, while empty containers of the non-clean type must be sent to the treatment and care areas in order to receive non-clean material here, and this transport will typically occur on the transport route for non-clean material.

It is preferred, according to an embodiment, that each container's position and filling state is constantly registered in the computer system such that it can hereby be ensured that there does not occur transport of non-clean material on the transport routes for the clean material and opposite.

According to an embodiment, input possibilities of different types belong to the computer system: it can be directly from a user via ordinarily known user interface; it can be via communication to the computer system of changed states on the hospital's treatment and care areas, and finally it can be communication to the computer system of registrations of scheduled changes in states of the hospital's treatment and care areas.

The computer system thus integrates, in one or another extent, with the possible patient and treatment oriented systems, which are to be found in advance in a hospital. Hereby, the workload is reduced for the staff, since many tasks, such as ordering of food, ordering of treatment items, ordering of linen and much else can occur automatically, when for example a patient is enrolled or an operation is planned and the data is entered into an IT-system. Together with well-known user orders, this system provides an especially comprehensive flexibility.

According to an embodiment, the user has, during the use of a simple user interface, possibility of submission of simple orders, but the computer system additionally has the feature that it can prompt users, who register a change on a specific department, for example registration of a patient, and ask the user to actively consider a number of questions about possible future deliveries linked to the patient, such that the computer system actively helps to ensure that all necessary materials are present for receiving a patient in a care and treatment department.

According to an embodiment, there is to the computer system connected a surveillance facility for each transport container such that the impacts that the container receives during the transport can be registered and passed on to a user. Hereby, a user becomes capable of determining if the transport has had negative impact on the transported material. In some cases, this can even be especially decisive for the material's applicability and this function is therefore quite important, especially in hospital environments.

Figure 2:
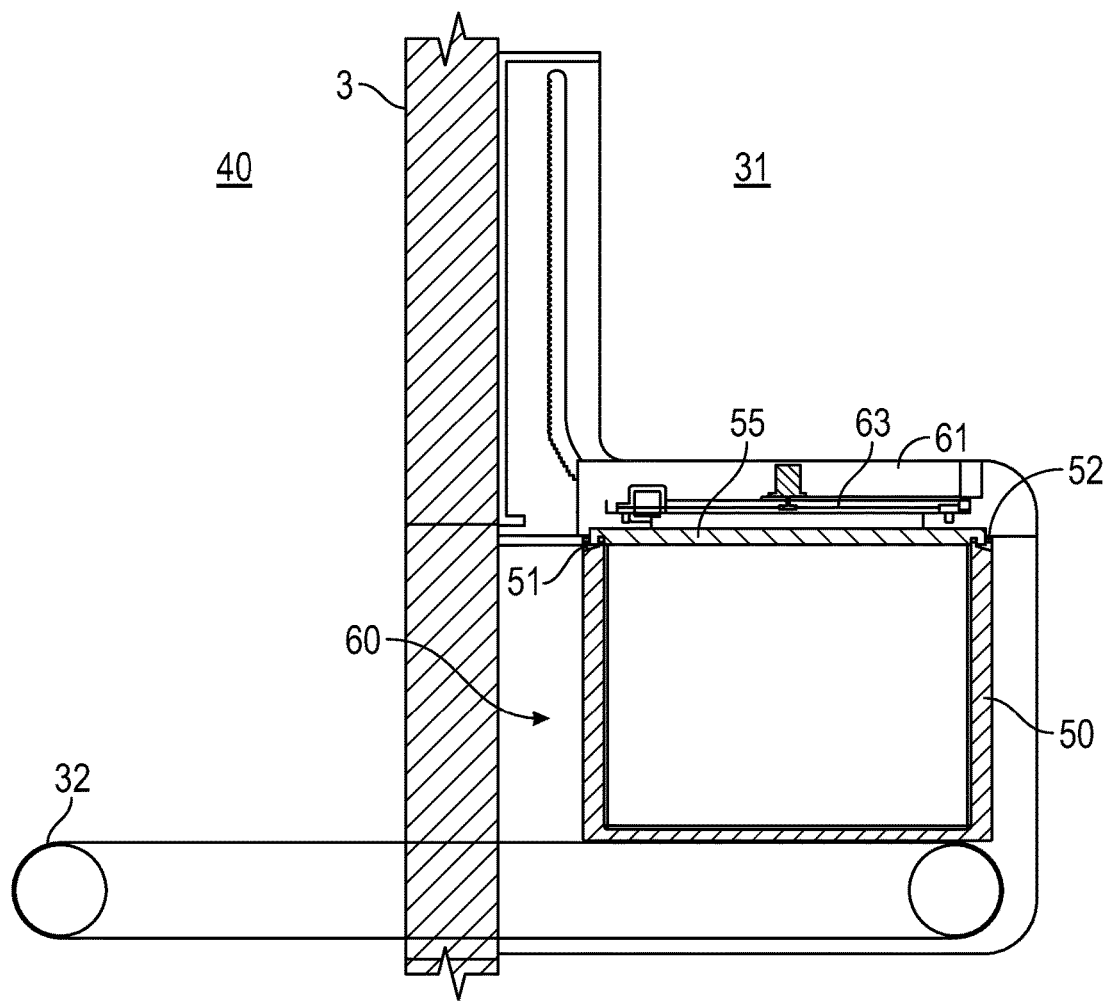
Figure 3:
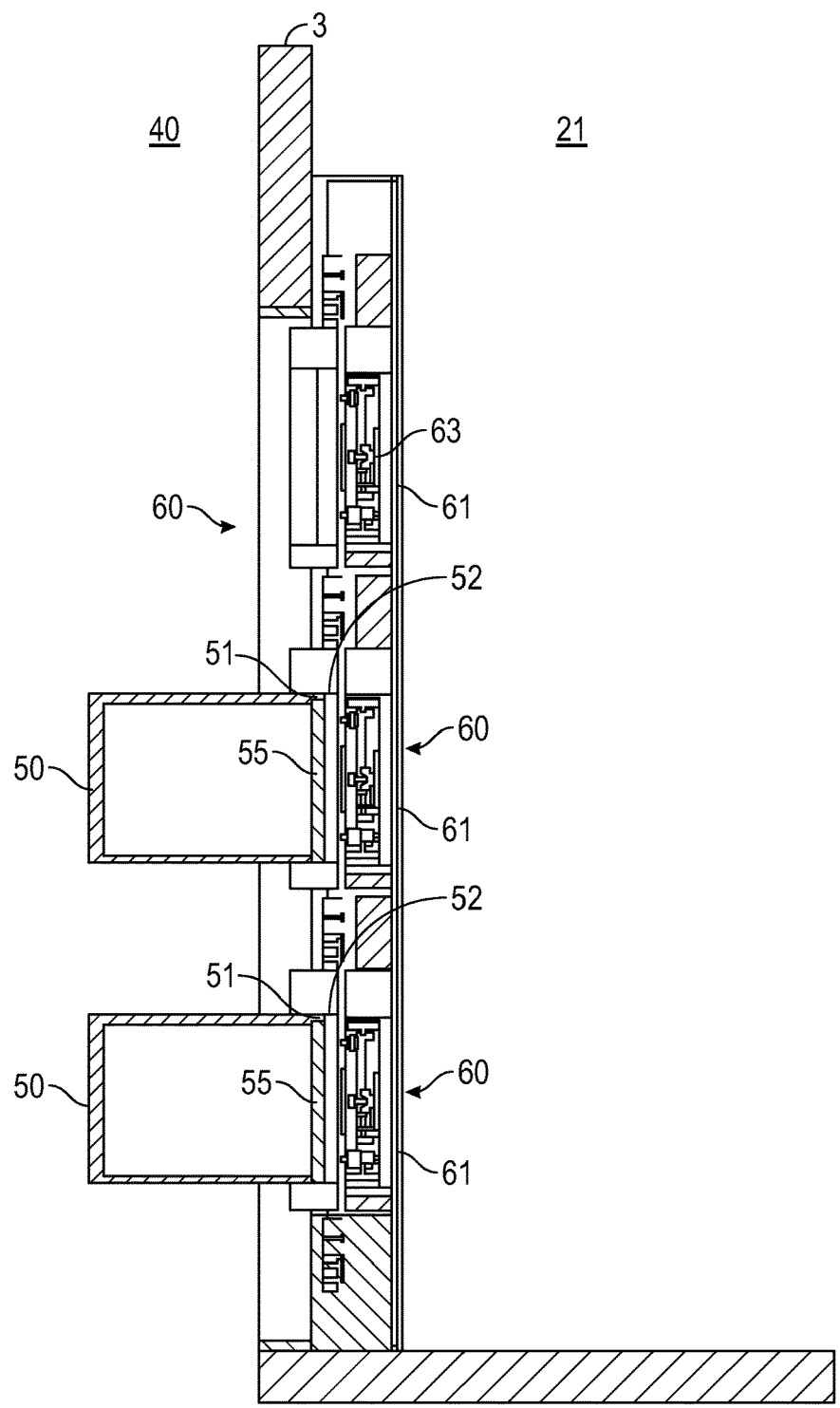
Figure 4:
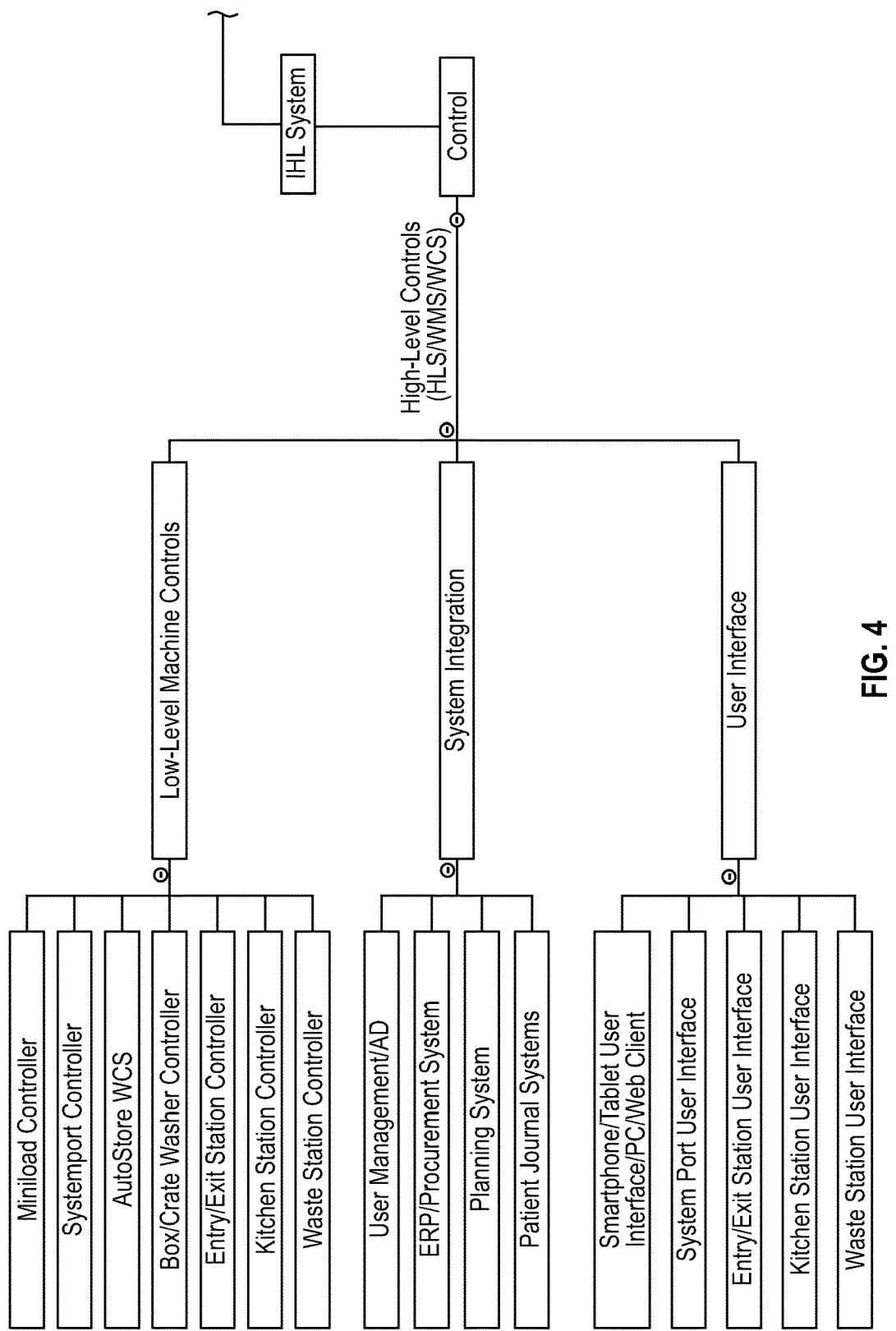
Figure 5:
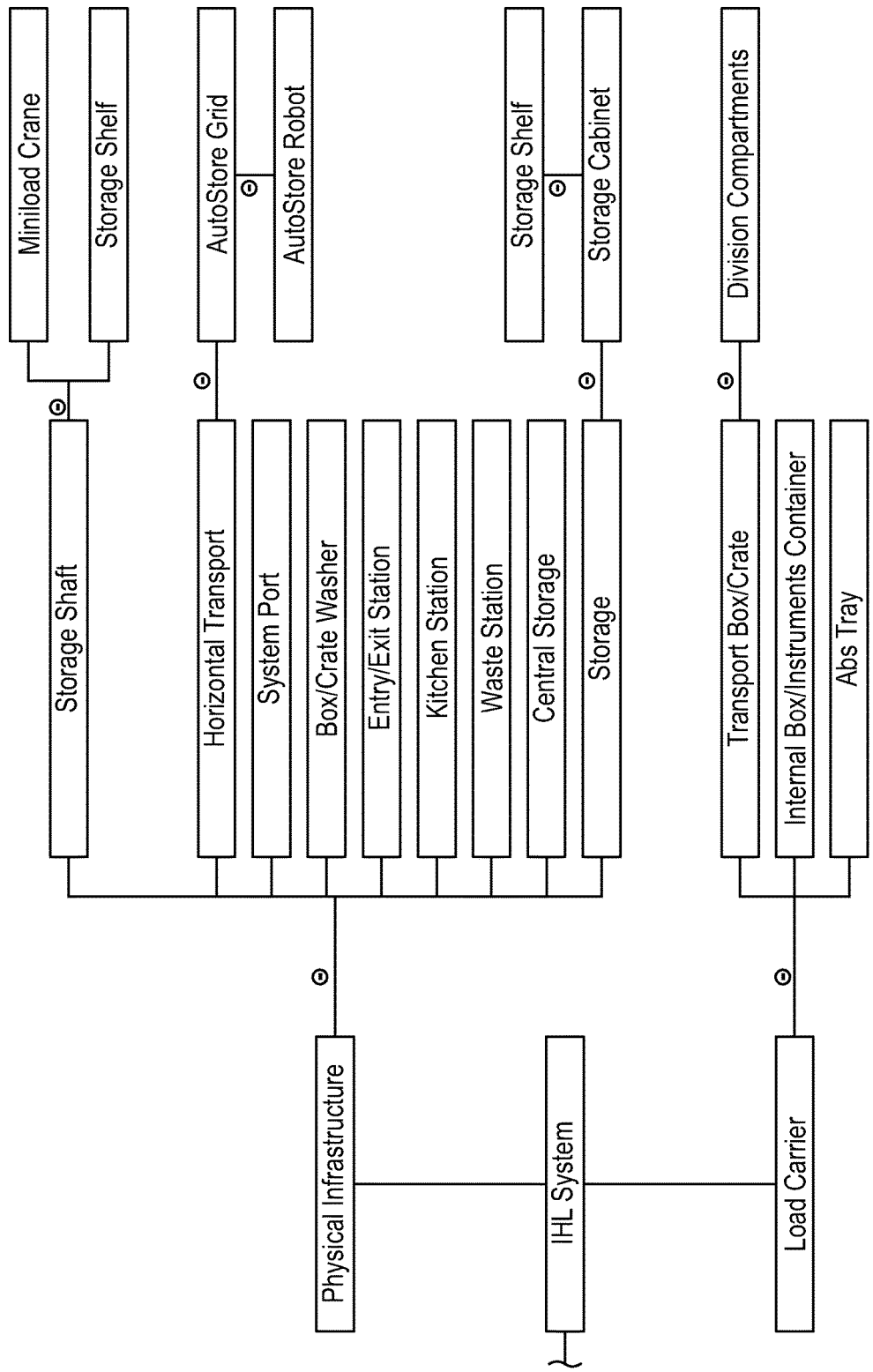
Figure 6:
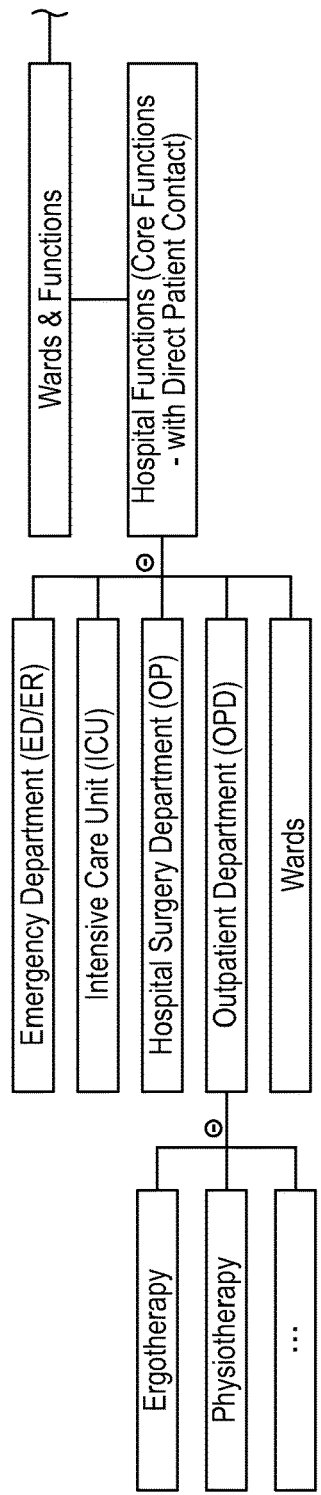
Figure 7:
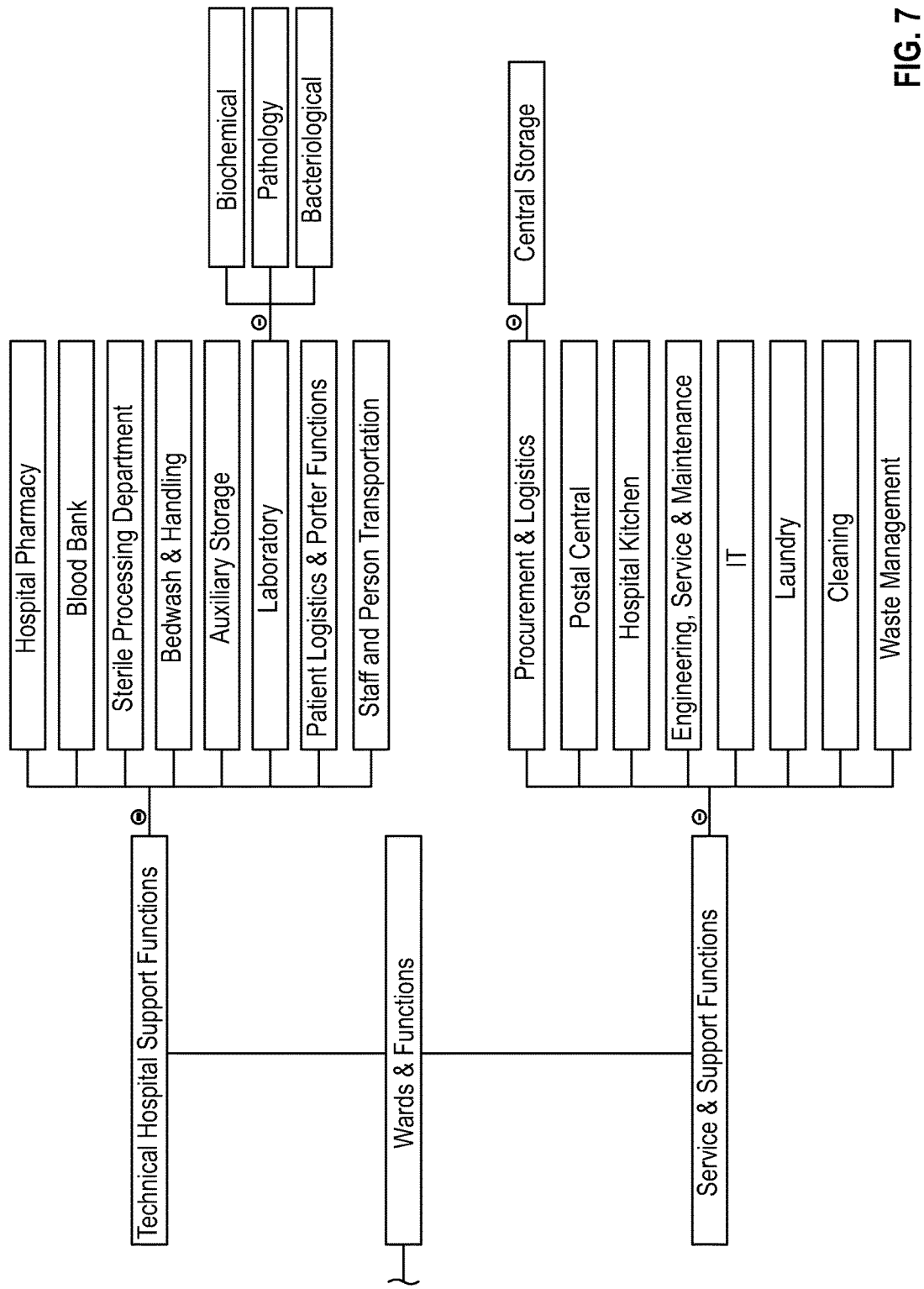

The invention will now be explained more fully with reference to the drawings, on which:

FIG. 1 shows a schematic overview of a transport and storage system,

FIG. 2 shows a cut through a schematic production of a partition with a lock gate, FIG. 3 shows a cut through a schematic production of a partition with another type of lock gate, FIG. 4 is a schematic depiction of the most important functional elements in a computer system for a transport and storage system, FIG. 5 is a schematic view of the most important physical elements, which a computer system, corresponding to the one in FIG. 4 will include, FIGS. 6 and 7 show a hierarchic presentation of the most common departments and functions, which characterize a modern hospital.

In FIG. 1 is seen a transport and storage system for servicing of a number of treatment and care areas, here named ward 1a, 1b, 2a, 2b, 3a and 3b. in a hospital 10. To each of the wards 1a-3b is connected a clean transport route 20. This transport route 20 is reserved for transport of clean goods to or from the treatment and care area 1a-3b such that only clean goods, which have not found any use in a treatment and care area, are transported here. The transport route 20 is indicated with two-way arrows, and it can be an indication of empty containers having to be sent with this route back to the filling place. Furthermore, it is for example possible to move a container from a department to another by this way, and then at least some of the transport route will be away from a ward. Simultaneously, there is a non-clean transport route 30, which is reserved for transport of non-clean goods. It will typically be goods, which have been in use, trash, biological samples and other, which come from one of the care and treatment areas and must go another place. Via the non-clean transport route, empty containers must however also be sent forward to all lock gates for the clean goods. As it is seen on the figure, the two transport routes 20, 30 are separated even though they occur in the same room. This means that if the accident should occur and a part of the transport route to non-clean material should become contaminated with contagious substances, then there will not occur spreading hereof to the other wards, since all transport towards the wards occurs on another transport route. It results in a significantly increased safety against spreading of pathogenic items from ward to ward. Also, it is relatively easy to isolate a single ward from the rest, since the majority of the transport of materials to and from the wards occurs via the invention's transport and storage system.

Certain types of goods, for example beds and other larger items cannot be sent with the transport system, as it is dimensioned according to the example here, but for wards where there is need for extra isolation of the patients, there can relatively easily be established systems, which prevent unnecessary transport of such items.

A system, as the shown, makes it significantly easier for a hospital 10, which observes epidemic outbreak of for example multi-resistant bacteria to control the outbreak and reschedule the operation such that there does not occur goods and personnel transport between wards such that the outbreak is isolated and is not spread in larger parts of the hospital.

As shown in FIG. 1, there is defined a cleanroom 21 for receiving goods on the ward and a dirty room 31 for shipping of goods from a ward. It is hereby ensured that the two flows of goods do not come into contact with each other. As it is seen, there is a two-way arrow from each ward 1a-3b to a cleanroom 21 and it indicates that the possibility of sending clean goods from one ward to another is present in the system if it is found to be sound. Hereby, the flexibility becomes larger and it has especially importance for the total amount of goods, which can be kept low, when wards can use from each other's stored goods. From the wards and towards the dirty room 31 there is, however, only one one-way facing arrow, which indicates that wards never receive goods from that way.

Between the different wards 1a, 2a, 3a and 1 b, 2b, 3b, there is led a shaft 40 named "miniload storage-shaft" and this indicates that here could have been created vertical stack facilities, where goods can be stored temporarily until further use on the wards. Such an arrangement could also be established in horizontal plane along a number of wards, which are situated side by side. Also, the two transport routes 20 and 30 will be established in this shaft 40.

In FIG. 1, there is in horizontal plane below the different wards, indicated a horizontal transport route 45 marked "Supply hallway/basement" and herein is placed a horizontal area 46 marked "AutoStore rail net". This should be understood as a more spacious storage area for, for example, clean goods. Furthermore, there is indicated a number of rooms o1, o2 marked "OP/treatment department" and here, there will typically be arranged operation, or other treatment facilities. Also for these rooms are connected both a clean room for reception of clean goods and a non-clean room for sluicing of used goods.

Offices and outpatient departments are likewise indicated with associated lock gates such that there is also from these areas access to the storage and transport system.

As shown in FIG. 2 and in FIG. 3, there is additionally, according to the invention, a separation between ward and transport routes, since a partition 3 is provided between the transport routes 20, 30 and the treatment and care areas o1, o2, 1a, 1b, 2a, 2b, 3a, 3b. Partitions 3 ensure that infectious items cannot spread from treatment and care areas and out on the transport routes 40, 45, 46. In the partitions 3, there must necessarily be a lock gate 60 or similar, as explained in the following.

The lock gates 60 shown in FIG. 2 and FIG. 3 are somewhat different, but they have the common feature that they allow a container 50 with an external opening brim 51 to fit tightly along this opening brim 51 to an internal opening brim 52 in lock gate 60 and that the transport routes 20, 30 include a conveyor 32 for containers 50, which conveyor 32 is connected to the lock gate 60. For the sake of clarity, the clean conveyor in FIG. 3 is left out. As it is seen in FIG. 2, the container 50 is presented in the lock gate 60 with its container brim in horizontal and the container can now receive material from above and down in the container. It is especially useful for material such as waste or used items, which are to be transported away from a ward and this lock and container type is then used as connection to non-clean transport route from the non-clean room. This type of container and lock gate is also applicable to biological samples from patients, since such samples are considered to be contaminated material, and should consequently use the non-clean transport route. In FIG. 2 is also shown a conveyor 32 which is designed to bring a container 50 into position in lock gate 60. In general, there is from the lock gate thus only access to the interior of a container 50, while a closure device 61 in the lock gate 60 is held closed as long as there is no container 50 put into position. It is hereby ensured that there is not, from the ward, access to the transport route behind the partition. The lock gate and the closing device are not described in detail here.

In FIG. 3 is shown a slightly different type of lock gate and transport container, where the container has its opening brim 51 placed along a vertical surface. Accordingly, an inner horizontal surface neighbours upon the container's opening and is the natural resting surface for material placed in the container 50. This type of container and lock is then used in connection to the clean transport route. Again, it is ensured that there from the ward is only access to the container's inner, since a closed blocks the access to the lock unless a container is provided with its container brim abutting on the lock gate's opening brim 52. In FIG. 3, the conveyor is not shown on the, towards the transport routes facing, side of the partition 3, but there will be usual transport devices or conveyors belonging to each of the 3 shown lock openings, of which only the two lowermost are fitted with containers 50 in the shown situation.

In both FIGS. 2 and 3, it is seen that the containers 50 have a, to the container brim, tightly fitting lid 55. A form-fitting engagement between container brim and the lid is accomplished by use of a gasket and suited locking pawls, as it is well known in the area. The lid 55 is designed to be removed automatically in the lock, whereby the container's inner is made accessible from the ward. Removal and re-attachment of the lid occurs with assistance from a gripper 63, which is indicated in FIG. 2 and FIG. 3, but otherwise not described in more detail.

The different arrangements: separated transport routes for clean and non-clean transport, lock gates and containers with the tight-fitting lids, and finally lock gates, for presentation of the containers' inner, each provide a contribution to lowering the risk of transport of infectious material from ward to ward and in total they also provide a very flexible and secure contribution to the total logistics in a hospital.

As mentioned, a first type of containers is used on the transport route, which is reserved for delivery of goods to the treatment and care area, the clean transport routes, and another type of containers on the transport route, which is reserved for removal of goods from the treatment and care area, the so-called non-clean transport routes. The transport container, with opening in a vertical surface is beneficial to all clean material, since this is often well-organized and for example bundled or pre-packed, and from a supplier, one can specify packing size or parcel, which fits the transport container's dimensions. The same applies for the non-clean material, which is to be sent away from a department. Here, the material will mostly not be pre-packed and not arranged, and a container with opening in an upper horizontal surface will be preferred.

The invention also includes a computer system, and here, all transport routes and all storage areas for containers, will be in connection with a computer system, and it is the computer system, which emits signals to start any transport route for moving of a container along it. Here, the clean transport routes are initiated for transport of containers with clean material and correspondingly, non-clean transport routes are started for transport of containers containing non-clean material.

An illustration of an intelligent hospital logistics system is presented in FIG. 4 and FIG. 5, where FIG. 4 shows the control functions' hierarchical structure, and FIG. 5 lists the belonging physical elements. Thus, the control includes a computer system, which in the outermost level includes machine control functions, system integration and user interfaces. As part of machine control functions are here listed: Miniload Controller, Systemport Controller, Autostore WCS, Crate washing Controller, Entry/Exit station Controller, Kitchen station Controller, Waste station Controller. Each of these controllers handles a specific task related to containers in the device, for example, the Miniload Controller will have to move a container from point A to point B, and if the miniload unit in question is for example a self-propelled unit, both point A and point B can be one of a plurality of possible receivers or deposit points. More simple transport units can be part of the system, such as for example an ordinary conveyor, but here, this will most often be fully automatic, such that the registration of a load a specific place, automatically makes the conveyor run and it then stops for example when the cargo is registered as arrived to a specific end point. By system port controller should be understood the control functions, which ensure that the lock gates function according to the regulations and correctly execute the containers' presentation on the hospital departments for either receiving or submitting material.

There also belongs an autostore or automatic stockroom to the system. It can typically be a stacking storage, which is well known and will not be described further. To a larger such autostore, there can be connected sectional partial storages, which are placed in immediate proximity of lock gates. Here, materials which must be quickly accessible can be placed, such that there does not pass much time from ordering to receiving, subsidiary for non-clean material, containers can temporarily be accumulated, for example in empty state, such that they are ready for receiving material in almost the same moment there is need for it.

Additional controllers belong to crate washing, to kitchen station and to waste station. Finally, entry/exit should be mentioned, where containers are filled up and made ready for storage in the autostore system, and are secondarily emptied for content, which from one or another reason has not found use, for example as a result of exceeding shelf service life. Finally, there can here occur shipping of containers to receivers, which have not got anything to do with the hospital.

In total, this computer system means that changes in a container's position and filling state are always registered in the computer system.

The computer system is, as further shown, integrated with several of a hospital's additional systems, for example User management/AD, ERP/procurement system, planning system or patient journal systems. Such integrations make it possible for the computer system to further automate the hospital operation such that for example orders at various suppliers occurs automatically or deliveries for departments are automatically updated according to changes in the individual patient's condition or planned activities automatically results in supply of the necessary resources for a department.

Finally, user interfaces of different kinds should be mentioned, which are also included as a part of the computer system. It can be as decentralized units, such as smartphones, tablet, PC or web-client units. It could also be consisting of actual input units, for example directly connected to lock gates (in FIG. 4 mentioned as "System Port") or connected directly to other of the "Low-level Machine Controls" as listed in FIG. 4.

The computer system thus receives input from several different types of units: 1) users via a user interface; 2) registrations of changed states on the hospital's treatment and care areas 2) registrations of planned changes in states of the hospital's treatment and care areas.

It is a distinctive feature of the system that user input from users via a user interface includes simple instructions about a given delivery to a department of a given material, or order about transport of a given material from the department to a given beneficiary, but also includes order or input, where a user is prompted by the computer system regarding supply of equipment as a result of detected changes in conditions in the treatment and care area. This dialogue-oriented input form, where the computer system asks for additional specifications about an otherwise automated order, helps to ensure optimal and highly flexible operation.

In relation to a given transport of a container in the system, there will always be connected frames for which outer effects and which retention times in the system the content of the container allows without being damaged and therefore, the computer system has to any transport of a transport container along a transport route connected a time and/or temperature limit, such that a transport can always be carried out during observation of the predefined time or temperature limits for the content in the container. There can obviously be other parameters than time and temperature, for example moisture burden, radiation of different kinds and vibrations/shocks, which the content in a container must maximally receive during the transport. Here, the computer system must then plan a transport route and schedule, which are weighed in relation to these requirements and in relation to other transports. If not all requirements can be met, the system can then at least deliver a detailed report about the transport course. This provides, for example a department, which receives food or medicine a possibility of evaluating in which extent the transport has had negative effect on the quality of the received shipment. Also for example blood samples and other biological samples, which are sent via a non-clean transport can be more of less effected by the transport process, and the sample result must always be seen in the light of potential negative effects, which a specific sample would have received since it was selected.

As shown in FIG. 4, there also belongs a physical architecture to the system and this will always in some extent reflect the individual hospital and its layout. Here should for example be noted the following elements, Storage shaft, Horizontal transport, System port, Crate washer, Entry/Exit station, kitchen station, Waste station, Central storage, Storage. To the storage shaft also belongs for example a Miniload-crane and a Storage shelf. In the horizontal transport is included elements such as AutoStore Grid and Autostore Robot. And under Depot is found the elements depot closet and Depot shelf. These elements are thus found physically around the units belonging to the hospital and their locations and number will depend on the individual hospital's layout and design.

FIG. 6 and FIG. 7 show, in overview, the different functional parts of a hospital. In FIG. 6 is listed the core tasks, which will most often be connected to a hospital. There is thus specified: Emergency Department, Intensive care unit, Hospital surgery department, Outpatient department and finally the wards. As part of outpatient departments can typically be mentioned Ergotherpy, Physiotherapy but many others can occur. In this overview, there is focus on an ordinary hospital, but a similar transport and storage system can find use in care institutions such as hospices and care or retirement homes. FIG. 7 provides a schematic overview over the special support functions, which will typically be an integrated part of a hospital, here divided into Hospital professional support functions and Service & Support functions. Under the hospital professional support functions are listed the following: Hospital pharmacy, Blood Bank, Sterile processing department, Bedwash & handling, Auxiliary storage, Laboratory, Patient logistics & porter functions and Staff and person transportation. Different laboratories are mentioned under Laboratory, namely: Biochemical, Pathology and Bacteriological. The here mentioned are seen as the most common, but it is possible to place some of these functions outside the hospital and other functions such as recreational and healing outdoor rooms could be included. Of Service & support functions are listed the following: Procurement & logistics+Central Storage, Postal central, Hospital kitchen, Engineering, service & maintenance, IT, Laundry, Cleaning, Waste Management. The in FIGS. 6 and 7 shown overview is not necessarily exhaustive, but for all the mentioned components applies that there will be a need for logistics connection between them and the described transport and storage system will be significantly useful for binding these elements together in an operation related advantageous way while ensuring the special needs for hygiene, which are present in a hospital or similar institution.

TERMS

Ward 1*a*,1*b*, 2*a*, 2*b*, 3*a*, 3*b*.
Room O1, O2
Partition 3

Hospital 10
Clean transport route 20
Clean room 21
Non-clean transport route 30
Non-clean room 31
Non-clean conveyor 32
Shaft 40
Horizontal transport route 45
Horizontal area 46
Container 50
External opening brim 51
Internal opening brim 52
Lid 55
Lock gate 60
Closing device 61
Gripper 63

The invention claimed is:

1. A transport and storage system for servicing of a number of treatment and care areas in a hospital, comprising:
  a first transport route connected to each of the treatment and care areas, the first transport route being reserved for transport of clean goods to or from each of the treatment and care areas;
  a second transport route connected to each of the treatment and care areas, the second transport route being reserved for transport of non-clean goods to or from each of the treatment and care areas, wherein the first and second transport routes are separated from one another;
  a first partition provided between the first transport route and each of the treatment and care areas;
  a second partition provided between the second transport route and each of the treatment and care areas;
  wherein each of the first and second partitions includes a plurality of lock gates corresponding respectively to the treatment and care areas, and
  wherein each of the first and second transport routes include a conveyor for containers with lids, each conveyor being connected to the lock gates, the containers being configured to house the clean and non-clean goods transported by the first and second transport routes, respectively,
  wherein each of the containers has a brim, and each of the lock gates has an internal opening brim configured to surround the container brim,
  wherein each of the containers comprises a lid designed to engage with the container brim so as to enclose the goods placed within the container, and each of the lock gates includes a gripper configured to automatically remove the lid from the container such that the inside of the container is made accessible from one of the treatment and care areas when the container is led to the respective lock gate.

2. The transport and storage system of claim 1, wherein a first type of container with the opening brim placed along a vertical surface is used on the first transport route, and a second type of container with the opening brim placed along a horizontal surface is used on the second transport route.

* * * * *